(12) United States Patent
Heath et al.

(10) Patent No.: US 10,780,267 B2
(45) Date of Patent: Sep. 22, 2020

(54) APPARATUS FOR TOPICAL APPLICATION OF MATERIAL

(71) Applicant: UNIVERSITY OF STRATHCLYDE, Glasgow Strathclyde (GB)

(72) Inventors: David Heath, East Kilbride (GB); Barry Hochfield, East Kilbride (GB)

(73) Assignee: UNIVERSITY OF STRATHCLYDE, Glasgow (GB)

( * ) Notice: Subject to any disclaimer, the term of this patent is extended or adjusted under 35 U.S.C. 154(b) by 0 days.

(21) Appl. No.: 15/507,710

(22) PCT Filed: Sep. 2, 2015

(86) PCT No.: PCT/GB2015/052539
§ 371 (c)(1),
(2) Date: Feb. 28, 2017

(87) PCT Pub. No.: WO2016/034878
PCT Pub. Date: Mar. 10, 2016

(65) Prior Publication Data
US 2017/0239454 A1 Aug. 24, 2017

(30) Foreign Application Priority Data
Sep. 3, 2014 (GB) .................................. 1415611.1

(51) Int. Cl.
*A61N 1/32* (2006.01)
*A61N 1/04* (2006.01)
(Continued)

(52) U.S. Cl.
CPC ........... *A61N 1/327* (2013.01); *A45D 34/042* (2013.01); *A61M 35/003* (2013.01);
(Continued)

(58) Field of Classification Search
CPC . A61M 35/003; A61N 1/0412; A61N 1/0448; A61N 1/325; A61N 1/327; A61N 1/328
See application file for complete search history.

(56) References Cited

U.S. PATENT DOCUMENTS 5,019,034 A * 5/1991 Weaver ............... A61B 5/14514
604/20
5,318,514 A 6/1994 Hofmann
(Continued)

FOREIGN PATENT DOCUMENTS

EP 1459782 9/2004
EP 1568395 8/2005
(Continued)

OTHER PUBLICATIONS

International Search Report of Counterpart PCT International Application No. PCT/GB2015/052539.
(Continued)

*Primary Examiner* — Jenna Zhang
(74) *Attorney, Agent, or Firm* — Liu & Liu (57) ABSTRACT

The present invention relates to apparatus for topical application of material for cosmetic purposes (10). The apparatus for topical application of material (10) comprises measurement apparatus configured to measure a property of skin of a human or animal subject and actuating apparatus configured to change a permeability of the skin of the human or animal subject in dependence on the measured property of the skin. The apparatus for topical application of material (10) further comprises application apparatus configured to apply material for cosmetic purposes to the skin whilst substantially no iontophoretic current flows through the skin and after the permeability of the skin has been changed.

19 Claims, 5 Drawing Sheets

(51) Int. Cl.
  *A61M 35/00* (2006.01)
  *A45D 34/04* (2006.01)
(52) U.S. Cl.
  CPC ......... *A61N 1/0412* (2013.01); *A61N 1/0448* (2013.01); *A61N 1/325* (2013.01); *A61N 1/328* (2013.01); *A61M 2205/3327* (2013.01); *A61M 2205/50* (2013.01); *A61M 2205/8206* (2013.01)

(56) References Cited

U.S. PATENT DOCUMENTS

| | | | |
|---|---|---|---|
| 5,495,338 | A | 2/1996 | Gouriou et al. |
| 6,708,060 | B1 * | 3/2004 | Avrahami ................ A61N 1/30 600/372 |
| 9,007,588 | B1 | 4/2015 | Igarashi |
| 2004/0078278 | A1 | 4/2004 | Dauga et al. |
| 2004/0202685 | A1 | 10/2004 | Manzo |
| 2004/0267189 | A1 | 12/2004 | Mavor et al. |
| 2006/0130266 | A1 * | 6/2006 | Brown ................... A61B 17/20 15/329 |
| 2008/0194928 | A1 | 8/2008 | Bandic et al. |
| 2009/0025747 | A1 | 1/2009 | Edgar et al. |
| 2009/0318786 | A1 | 12/2009 | Blank et al. |
| 2010/0241057 | A1 | 9/2010 | Pak et al. |
| 2011/0264173 | A1 * | 10/2011 | Flyash ............... A61N 1/36031 607/62 |
| 2011/0319971 | A1 | 12/2011 | Zemmouri et al. |
| 2012/0190956 | A1 * | 7/2012 | Connolly ............ A61F 13/0253 600/372 |
| 2012/0316381 | A1 | 12/2012 | Teggatz et al. |
| 2013/0345616 | A1 | 12/2013 | Chang |
| 2014/0378887 | A1 * | 12/2014 | Chang .................. A61N 1/0472 604/20 |
| 2015/0272501 | A1 | 10/2015 | Maceachern et al. |

FOREIGN PATENT DOCUMENTS

| | | | |
|---|---|---|---|
| EP | 2152358 | | 3/2011 |
| EP | 2319445 | | 5/2011 |
| EP | 2335576 | | 6/2011 |
| EP | 2548610 | | 1/2013 |
| EP | 2548610 | A1 * | 1/2013 ........... A61N 1/0448 |
| EP | 2548610 | A1 * | 1/2013 ........... A61N 1/0448 |
| JP | 2007-159950 | | 6/2007 |
| RU | 2038101 | | 6/1995 |
| RU | 96102225 | | 5/1998 |
| WO | 89/06555 | | 7/1989 |
| WO | 95/26781 | | 10/1995 |
| WO | 99/60377 | | 11/1999 |
| WO | 00/27473 | | 5/2000 |
| WO | 00/35357 | | 6/2000 |
| WO | 2004/112689 | | 12/2004 |
| WO | 2008/072237 | | 6/2008 |
| WO | 2010/093503 | | 8/2010 |
| WO | 2011/112248 | | 9/2011 |
| WO | 2015/021446 | | 2/2015 |
| WO | 2017/109519 | | 6/2017 |

OTHER PUBLICATIONS

International Search Report of Counterpart PCT International Application No. PCT/GB2016/054075.

* cited by examiner

APPARATUS FOR TOPICAL APPLICATION OF MATERIAL

FIELD OF THE INVENTION

The present invention relates to apparatus for topical application of material for cosmetic purposes and a method therefor.

BACKGROUND ART

Apparatus which measure properties of the skin and provide guidance on application of cosmetics are known. For example, US 2004/0202685 A1 describes a process of determining skin structure for the purpose of identifying and formulating skin care products that address deficiencies observed in the skin. The skin structure is determined by measuring skin moisture content, sebum content, skin firmness, thickness and elasticity, transepidermal water loss and skin pH and by performing photo analysis of the skin with UV and visible light. In WO 2004/112689 there is recognition that it is advantageous to enhance the penetration of cosmetics into the skin and to increase their bioavailability when in the skin. WO 2004/112689 describes apparatus comprising electrode pairs which are operative to generate sparks close to the skin. The thus generated sparks form micro-channels in the skin by ablation. When a cosmetic is applied subsequently by hand, the micro-channels provide for improved uptake and effect of the applied cosmetic.

The present inventors have become appreciative of the important role played by skin permeability in application of cosmetics. In addition the present inventors have recognised that whether or not an increase in permeability or indeed whether or not a particular extent of increase in permeability is desirable depends on skin type. The present inventors have further recognised that the properties of a particular person's skin change from one time to another with such change having a bearing on the effectiveness of changing skin permeability prior to application of a cosmetic.

It is therefore an object for the present invention to provide apparatus for topical application of material to the skin for cosmetic purposes in which the apparatus provides for improved efficacy of the applied material having regard to permeability of the skin. It is a further object for the present invention to provide a method of topically applying material for cosmetic purposes in which the method provides for improved efficacy of the applied material having regard to permeability of the skin.

STATEMENT OF INVENTION

According to a first aspect of the present invention there is provided apparatus for topical application of material for cosmetic purposes, the apparatus comprising:
  measurement apparatus configured to measure a property of skin of a human or animal subject;
  actuating apparatus configured to change a permeability of the skin of the human or animal subject in dependence on the measured property of the skin; and
  application apparatus configured to apply material for cosmetic purposes to the skin whilst substantially no iontophoretic current flows through the skin and after the permeability of the skin has been changed.

The apparatus for topical application of material for cosmetic purposes apparatus comprises measurement apparatus which is configured to measure a property of skin of a human or animal subject. The permeability of the skin, for example, may be determined in dependence on the measured property. The apparatus further comprises actuating apparatus which is configured to change a permeability of the skin of the human or animal subject in dependence on the measured property of the skin. The measured property, for example, may be such that it is determined that an increase in permeability is desirable with the actuating apparatus being operative accordingly to increase the permeability of the skin. The apparatus yet further comprises application apparatus which is configured to apply material for cosmetic purposes to the skin whilst substantially no iontophoretic current flows through the skin and after the permeability of the skin has been changed. The apparatus for topical application of material is thus capable of itself of measuring a property of the skin, acting in dependence thereon by changing a permeability of the skin and then applying material to the skin. By way of example, the apparatus for topical application of material may be operative to measure the property of the skin after actuation and decide that more actuation is required before application of material for cosmetic purposes. In contrast with the prior art mentioned above, apparatus according to the invention is operative to change the permeability of the skin in dependence on measurement of a property of the skin before material is applied to the skin. The apparatus of WO 2004/112689 is operative to change the permeability of skin irrespective of a property of the skin and thus, for example, may increase the permeability when no increase is required or may increase the permeability by more or less than is required.

Apparatus according to the present invention is for topical application of material for cosmetic purposes. The apparatus for topical application of material for cosmetic purposes therefore may be configured to apply material topically for cosmetic purposes. Furthermore the apparatus may be configured to apply material for cosmetic purposes to an external surface of the skin. The actuating apparatus may be configured to change a permeability of skin, such as of an area of skin, which has been subject to measurement by the measurement apparatus. Alternatively or in addition the application apparatus may be configured to apply material to skin, such as to an area of skin, which has been at least one of: subject to measurement by the measurement apparatus; and subject to change in permeability by the actuating apparatus.

As mentioned above, the actuating apparatus is configured to change a permeability of the skin. The change in permeability of the skin may affect at least one of: a rate of penetration of applied material into the skin; a depth from an external surface of the skin to which an applied material penetrates; an extent to which applied material travels below the surface of the skin in a direction orthogonal to the surface of the skin; and whether or not an applied material, such as a material of particular composition comprising particles or molecules of greater than a certain size, travels from a surface of the skin into the skin. The change in permeability of the skin may be a change in physical permeability of the skin.

The actuating apparatus may be configured to change a permeability of the skin by application of an electric signal to the skin. The electric signal may be at least one of substantially constant and varying, such as at least one pulse. The actuating apparatus may be configured to change a permeability of the skin by application to the skin of at least one of: an electric potential signal; and an electric current signal. As described further below, the electric potential signal and the electric current signal may be applied to the skin at one of: different times; and substantially a same time.

In certain forms, the electric potential signal may be applied to create pathways and then the electric current signal may be applied to maintain the created pathways. Therefore the actuating apparatus may be configured to apply the electric potential signal and then to apply the electric current signal.

The application of an electric potential to the skin has been found to increase permeability of the skin. Moreover the increase in permeability is normally reversible such that following ceasing of application of the electric potential the permeability returns substantially to the level before application of the electric potential. The actuating apparatus may comprise spaced apart members which are susceptible of carrying current and which are operative to develop an electric potential therebetween. Each spaced apart member may have the form of an electrode. The electrodes may be disposed in substantially the same plane whereby the electrodes present a substantially planar surface that can abut against the skin. A spaced apart member may be formed from copper. The spaced apart member may be covered at least in part with zinc and more specifically gold. The actuating apparatus may be configured such that the spaced apart members are electrically isolated from the skin when the actuating apparatus bears against the skin. The actuating apparatus therefore may comprise an electrically insulating material, such as polyurethane, which covers the spaced apart members to thereby provide for electrical isolation.

The application of an electric potential to the skin to increase permeability is termed electropermeabilisation or sometimes electoporation. Electropermeabilisation involves changes in membranes of skin cells which occur when a sufficiently large trans-membrane electric potential is applied. An electric potential in the range of 0.5 to 1 Volt has been found to suffice for a cell membrane in many circumstances. The applied electric potential overcomes the cell's trans-membrane potential and thereby induces structural rearrangement and loss of semi-permeability of cell membranes on account of formation of pathways to thereby provide for increased permeability. As mentioned above, pathway formation is normally reversible following removal of the applied electric potential. The approach according to the present invention therefore may result in substantially no irreversible change in permeability and, in contrast with the approach of WO 2004/112689, no destruction of or no appreciable damage to cells.

The stratum corneum typically has up to about 100 multi-lamellar bi-layers and may thus require an electric potential of 100 Volts to achieve electropermeabilisation where each bi-layer requires an electric potential of 1 Volt to achieve electropermeabilisation. The actuating apparatus therefore may be configured to apply an electric potential of at least 20 Volts, 30 Volts, 40 Volts, 50 Volts, 60 Volts, 70 Volts, 80 Volts, 90 Volts, 100 Volts, 110 Volts, 120 Volts, 130 Volts or 140 Volts. Application of an electric potential above a certain level may be undesirable under certain circumstances. More specifically the stratum corneum may comprise fewer bi-layers and an unduly high electric potential may reduce an extent of reversibility or cause appreciable damage to cells. Furthermore apparatus according to the present invention may be configured to provide for intra-dermal delivery of material in view of the cosmetic nature of the material and in contrast to other potential applications in which trans-dermal delivery of material may be desired. The actuating apparatus therefore may be configured to apply an electric potential of no more than 150 Volts, 140 Volts, 130 Volts, 120 Volts, 110 Volts, 100 Volts, 90 Volts, 80 Volts, 70 Volts, 60 Volts, 50 Volts or 40 Volts. The actuating apparatus may be configured to change a level of applied electric potential. The level of applied electric potential may be changed, for example, to take account of different skin thicknesses and types. Alternatively the level of applied electric potential may be changed in dependence on measurement of a property of the skin as described elsewhere herein.

The energy delivered to the skin is a function of the electric potential and the duration of its application to the skin. It may be desirable to have a certain level of energy delivered to the skin. A sufficiently high level of electric potential and therefore level of energy may be required to achieve the desired electropermeabilisation. On the other hand an unduly high level of energy may be undesirable in that it may cause discomfort or perhaps even cell damage. The actuating apparatus may be configured to apply the electric potential signal to the skin as a pulse. Application of a pulse may provide a sufficient level of electric potential whilst limiting the level of energy. A width of the pulse may be at least 2 µs, 5 µs, 10 µs, 20 µs, 50 µs, 100 µs, 250 µs, 500 µs, 1 ms, 10 ms, 25 ms, 50 ms, 75 ms or 100 ms. A width of the pulse may be no more than 125 ms, 100 ms, 75 ms, 50 ms, 25 ms, 10 ms, 1 ms, 500 µs, 250 µs, 100 µs, 50 µs, 20 µs, 10 µs or 5 µs. The actuating apparatus may be configured to change at least one of duration of the applied pulse and a time period between applied pulses. The duration of the applied pulse may be changed, for example, to take account of different skin thicknesses and types. The time period between applied pulses may be changed, for example, to take account of different skin thicknesses and types. Alternatively at least one of the duration of an applied pulse and the time period between applied pulses may be changed in dependence on measurement of a property of the skin as described elsewhere herein. The duration of the pulse, the time period between applied pulses and perhaps also the level of the pulse as described above may be determined to provide a desired effect, such as in respect of a diameter of pathways formed in the skin or density of pathways formed in the skin.

Where the actuating apparatus is configured to generate an electric potential signal in the form of a pulse, the actuating apparatus may be configured such that the pulse decays progressively from a peak value. More specifically the pulse may decay exponentially. Having a pulse which decays progressively and more specifically exponentially may provide for a delay in reversal of pathway formation to thereby prolong increased permeability of the skin. Alternatively or in addition and as described below the actuating apparatus may be configured to apply an electric current signal to the skin.

A separation between the spaced apart members of the actuating apparatus may determine an extent of an electric field generated by the actuating apparatus. An extent of the electric field may determine a depth in the skin to which the field penetrates. The separation may be at least 5 µm, 10 µm, 20 µm, 50 µm, 100 µm, 200 µm, 400 µm, 600 µm, 800 µm, 900 µm or 1 mm. A width of a spaced apart member may be in accordance with the figures specified in the immediately preceding sentence. The separation may be no more than 1.1 mm, 1 mm, 900 µm, 800 µm, 600 µm, 400 µm, 200 µm, 100 µm, 50 µm, 20 µm, 10 µm or 5 µm. A width of a spaced apart member may be in accordance with the figures specified in the immediately preceding sentence. A spaced apart member may be elongated. A spaced apart member may define a non-linear path such as a serpentine path. The spaced apart members may have an interdigitated structure. As mentioned above each spaced apart member may have the form of an electrode.

The application of an electric current to the skin has been found to increase permeability of the skin. Moreover the increase in permeability is normally reversible such that following ceasing of application of the electric current the permeability returns substantially to the level before application of the electric potential. The actuating apparatus may comprise spaced apart current applying members which carry current and which are operative to pass current therebetween by way of the skin when the spaced apart current applying members are in contact with the skin. The actuating apparatus may be configured such that the electric current is substantially constant while it is being applied to the skin. Each spaced apart current applying member may have the form of an electrode. Each electrode may lack the insulating layer described above with reference to electric potential application to thereby provide a conductive path between the electrode and the skin. The current applying electrodes may be disposed in substantially the same plane whereby the current applying electrodes present a substantially planar surface that can abut against the skin. A spaced apart current applying member may be formed from copper. The spaced apart current applying member may be covered at least in part with zinc and more specifically gold. Each spaced apart current applying member may define an area having a non-linear profile which is rounded. The spaced apart current applying member may therefore lack sharp edges. Each spaced apart current applying member may define an area which is substantially semicircular.

Application of electric current to the skin typically reduces the impedance of the skin with the impedance being a function of duration of application of the electric current and density of the electric current. Decreased skin impedance normally reflects increased permeability of the skin on account of changes to the skin caused by the flow of electric current. The increase in permeability and reduction in impedance is understood to be because of recruitment of appendageal pathways as transport pathways. This phenomenon is normally termed iontophoresis. Current flowing during iontophoresis is termed iontophoretic current. In contrast with application of electric potential, application of electric current provides for movement of the material for cosmetic purposes along the pathways.

The actuating apparatus may be configured to develop by way of the spaced apart current applying members an electric potential therebetween of no more than 50 Volts, 40 Volts, 30 Volts, 20 Volts, 10 Volts, 5 Volts, 2 Volts or 1 Volt. The actuating apparatus may be configured to develop by way of the spaced apart current applying members an electric potential therebetween of at least 0.5 Volts, 1 Volt, 2 Volts, 5 Volts, 10 Volts, 20 Volts, 30 Volts or 40 Volts. The actuating apparatus may be configured such that a current is passed through the skin of no more than 500 $\mu A/cm^2$, 400 $\mu A/cm^2$, 300 $\mu A/cm^2$, 200 $\mu A/cm^2$, 175 $\mu A/cm^2$, 150 $\mu A/cm^2$, 125 $\mu A/cm^2$, 100 $\mu A/cm^2$, 75 $\mu A/cm^2$, 50 $\mu A/cm^2$, 25 $\mu A/cm^2$, 10 $\mu A/cm^2$ or 5 $\mu A/cm^2$. The actuating apparatus may be configured such that a current is passed through the skin of at least 1 $\mu A/cm^2$, 5 $\mu A/cm^2$, 10 $\mu A/cm^2$, 25 $\mu A/cm^2$, 50 $\mu A/cm^2$, 75 $\mu A/cm^2$ 100 $\mu A/cm^2$, 125 $\mu A/cm^2$, 150 $\mu A/cm^2$, 175 $\mu A/cm^2$, 200 $\mu A/cm^2$, 300 $\mu A/cm^2$ or 400 $\mu A/cm^2$.

In certain embodiments, the application of an electric potential and an electric current to the skin may be used together in the apparatus to advantageous effect. An electric potential may be applied to the skin to create pathways therein and then application of the electric potential may cease while an electric current is applied to the skin to maintain the pathways created by the electric potential. The actuating apparatus may be configured accordingly. More specifically the actuating apparatus may comprise spaced apart members which are operative to apply the electric potential and spaced apart current applying members which are operative to apply the electric current. The spaced apart members may be disposed between the spaced apart current applying members, such as between a pair of current applying members. Alternatively or in addition, the actuating apparatus may be configured to selectively apply one of an electric potential and an electric current to the skin. For example under certain circumstances one of pathways through the stratum corneum and pathways through skin appendages may be preferred over the other.

As specified above the apparatus for topical application of material for cosmetic purposes, the apparatus comprises measurement apparatus configured to measure a property of skin of a human or animal subject. More specifically the measurement apparatus may be configured to measure an electrical property of skin of a human or animal subject.

The measurement apparatus may be configured to measure an impedance of the skin. Apparatus according to the present invention may be operative to make a determination in respect of permeability of the measured skin in dependence on the measured impedance. More specifically the apparatus may be operative to make a determination in respect of permeability in dependence on a real part of measured impedance. The apparatus may be operative to make the determination in dependence on a model which relates measured impedance and permeability to each other. The measured property of the skin may therefore comprise impedance and more specifically a real part of impedance. The measurement apparatus may comprise spaced apart measurement members and a signal generator, the signal generator being operative to apply a signal to the spaced apart measurement members. The spaced apart measurement members may have one or more features of the spaced apart current applying members described above. Therefore, for example, each spaced apart measurement member may be semicircular in area and lack an insulating layer with both spaced apart measurement members lying in substantially the same plane whereby the spaced apart measurement members may be placed against the skin. The apparatus for topical application of material for cosmetic purposes may be configured that the spaced apart measurement members and the spaced apart current applying members are constituted by the same components. The apparatus for topical application of material for cosmetic purposes therefore may be configured to selectively operate these same components to provide for one of measurement and actuation.

The signal generator may be configured to generate a varying signal (i.e. a first signal) such as an alternating current potential signal. More specifically the signal generator may be configured to change a frequency of a generated varying signal. The signal generator therefore may be operative to change the frequency between a low value and a high value. The frequency may be at least 1 Hz, 10 Hz, 50 Hz, 100 Hz, 250 Hz, 500 Hz, 1 kHz, 10 kHz, 50 kHz, 100 kHz, 250 kHz, or 500 kHz. The frequency may be no more than 1 MHz, 500 kHz, 250 kHz, 100 kHz, 50 kHz, 10 kHz, 1 kHz, 500 Hz, 250 Hz, 100 Hz, 50 Hz, or 10 Hz. The signal generator may be operative to change the frequency over plural ranges. Alternatively or in addition the signal generator may be configured to generate a varying signal comprising plural frequencies at the same time. A peak to peak voltage of the signal may be at least 5 mV, 10 mV, 25 mV, 50 mV, 100 mV, 150 mV, 200 mV or 250 mV. A peak to peak voltage of the signal may be no more than 500 mV, 250 mV, 200 mV, 150 mV, 100 mV, 50 mV, 25 mV or 10 mV. The measurement apparatus may thus apply a varying and more specifically alternating current signal to the skin. The measurement apparatus may further comprise a signal measurement arrangement which is configured to measure a current signal between the spaced apart measurement members. The signal measurement arrangement may be configured to determine an impedance in dependence on the measured current signal and the voltage signal applied to the skin. The signal measurement arrangement may be configured to determine at least one of: magnitude and phase of the impedance; and real and imaginary parts of the impedance. The signal measurement arrangement may be configured to determine a capacitance of the skin in dependence on the imaginary part of the impedance, the frequency of the signal and a model of the skin. More specifically the model of the skin may comprise a resistance value. The resistance value may represent a resistance of an outermost layer of the stratum corneum.

The measurement apparatus may be configured to measure a capacitive reactance presented by the skin. The measurement apparatus may therefore comprise spaced apart capacitance measurement members and a signal generator, the signal generator being operative to apply a signal (i.e. a second signal) to the spaced apart capacitance measurement members. The spaced apart capacitance measurement members may be configured such that they are electrically isolated from the skin when the spaced apart capacitance measurement members bear against the skin. The spaced apart capacitance measurement members therefore may comprise an electrically insulating material. The spaced apart capacitance measurement members may have one or more features of the spaced apart members described above. Therefore, for example, the spaced apart capacitance measurement members may have an interdigitated electrode structure. The apparatus for topical application of material for cosmetic purposes may be configured such that the spaced apart capacitance measurement members and the spaced apart members are constituted by the same components. The apparatus for topical application of material for cosmetic purposes therefore may be configured to selectively operate these same components to provide for one of measurement and actuation.

As described hereinabove the signal generator may be configured to apply a varying frequency signal of varying and more specifically alternating current form to the spaced apart capacitance measurement members. The measurement apparatus may further comprise a signal measurement arrangement which is operative to measure an impedance and more specifically capacitive reactance between the spaced apart capacitance measurement members. The measured property of the skin may comprise capacitive reactance. The measurement apparatus may be operative to determine at least one of capacitance and relative permittivity in dependence on the measured impedance. A thickness of the skin being measured may be determined in dependence thereon as described further below.

Apparatus according to the present invention may be operative to determine a relative permittivity. The relative permittivity may be determined in dependence on the impedance and more specifically capacitive reactance, frequency, an area of plates defining the capacitor and a distance separating the plates defining the capacitor. A permeability of the skin may be determined in dependence on at least one of the relative permittivity and the impedance. Alternatively or in addition the permeability of the skin may be determined in dependence on a distance separating the plates defining the capacitor. Where the measurement apparatus is operative according to both of the above described approaches (i.e. by way of the isolated and non-isolated electrodes), the apparatus according to the present invention may be operative to make a further determination based on measurements made by both approaches. More specifically the further determination may be in respect of an improved determination of a parameter relating to measurement, such as a distance separating the plates. A first value for a first parameter corresponding to capacitance, such as relative permittivity, may be determined in dependence on measurements made with the isolated electrodes. A value for capacitance (i.e. a second value) may be determined in dependence on measurements made with the non-isolated electrodes. A further value corresponding to capacitance, such as a distance separating the plates, may be determined in dependence on the first and second values.

The application apparatus may comprise a material actuator which is operative to dispense material for cosmetic purposes from the apparatus for topical application of material. The material actuator may comprise a pump. The application apparatus may comprise a reservoir which is configured to hold material for cosmetic purposes. The material actuator may be operative to dispense material for cosmetic purposes from the reservoir. The application apparatus may comprise at least one dispensing aperture through which material for cosmetic purposes is dispensed from the apparatus for topical application of material for application to the skin of the subject.

The at least one dispensing aperture may be disposed adjacent to at least one of the measurement apparatus and the actuating apparatus.

The material may be fluent material. The material may be fluid and more specifically a liquid albeit perhaps a viscous liquid such as a cream, paste, gel or foam.

Further to measurement apparatus as described hereinabove, the measurement apparatus may be configured to measure at least one further property of the skin. The measurement apparatus therefore may be configured to perform spectroscopic analysis of the skin. Spectroscopic analysis may comprise causing at least one of infrared and ultraviolet light to impinge on the skin and measuring light which is at least one of reflected and scattered by the skin. Thereafter the measured light may be analysed to provide data on a condition of the skin, such as permeability, which may, for example, be used to validate or correlate with data obtained by measurement as described hereinabove. In certain forms, the measurement apparatus may be operable on the basis of at least one of the presently described approaches and not in addition to the approach described hereinabove.

Further to actuating apparatus as described hereinabove, the actuating apparatus may be operable on the skin in at least one further different fashion. According to one approach, the actuating apparatus may be configured to cause an ultrasonic signal to impinge on the skin. The actuating apparatus therefore may comprise an ultrasonic transducer. According to an additional or alternative approach, the actuating apparatus may be configured to cause light, such as at least one of infrared light and ultraviolet light, to impinge on the skin. The actuating apparatus therefore may comprise a light source. Ultrasonic or light energy may be of beneficial effect, such as in respect of further increasing permeability or increasing blood flow. In certain forms, the actuating apparatus may be operable on the basis of at least one of the presently described approaches and not in addition to the approach described hereinabove.

The material may be of a particular constitution which is intended to effect an improvement such as in respect of the cosmetic appearance of the like of the skin of the face. The material therefore may be a substance. The material for cosmetic purposes may be a cosmetic agent. The material for cosmetic purposes may comprise at least one of: primer, concealer, foundation, bronzer, setting spray, cleanser, toner, skin-care lotion, moisturiser, humectant, sunscreen, tanning oil, tanning lotion, skin lightener and exfoliant.

The apparatus for topical application of material may be portable and more specifically hand portable. The apparatus for topical application of material may comprise a housing which contains and supports other components of the apparatus. The housing may be configured to be gripped in one hand whereby the apparatus for topical application of material may be brought into use in one hand and operated by one hand with perhaps the exception of operation of a user operable control where such is comprised in the apparatus. The housing may be elongated in form. At least one of the measurement apparatus, the actuating apparatus and the application apparatus may be disposed at or towards an end of the housing. The housing may be shaped so as to allow the housing be gripped by a user while the housing is received in the palm of the user's hand. More specifically the apparatus for topical application of material may be configured such at least one of the measurement apparatus, the actuating apparatus and the application apparatus may be brought adjacent the skin of the subject while being so gripped.

The apparatus for topical application of material may be configured to measure a property of the skin by way of the measurement apparatus before and/or after the actuating apparatus is operative. Thus the apparatus for topical application of material may be operative to measure the property of the skin to determine how the permeability of the skin has been affected by the actuating apparatus. The apparatus for topical application of material may be configured such that the measurement apparatus is operative after the actuating apparatus has ceased to operate. The actuating apparatus may operate further in dependence on further measurement. Alternatively or in addition the apparatus for topical application of material may be configured such that the measurement apparatus is operative during operation of the actuating apparatus.

The apparatus for topical application of material may be configured to at least one of measure a property of the skin and change a permeability of the skin after operation of the application apparatus. The apparatus for topical application of material therefore may be operative to apply an amount of material for cosmetic purposes to the skin before the measurement apparatus is operative to make further measurement of the skin to, for example, determine how a condition of the skin has changed in dependence on application of the amount of material. The actuating apparatus may then be further operative to change a permeability of the skin in dependence on the further measurement. There may thus be plural operation at spaced apart times of each of the measurement apparatus, the actuating apparatus and the application apparatus with an order of their operation and number of times of their operating depending on circumstances.

The apparatus for topical application of material may comprise data storage. The apparatus for topical application of material may comprise at least one of a user operable control and a data communication port. The data communication port may provide for at least one of wireless communication, such as in accordance with the WiFi standard, and wired communication, such as by way of a USB port. The user operable control may be configured for user operation whereby operation of the apparatus for topical application of material may be controlled by the user. The apparatus for topical application of material may be configured such that data may be received thereby by way of the data communication port from further apparatus, such as a computer. The received data may be stored in the data storage. Data stored on further apparatus, such as a computer may thus be uploaded to the apparatus for topical application of material. The data stored on the further apparatus may comprise at least one of: data from previous operation of the apparatus for topical application of material in respect of: previous measurement by the measuring apparatus; previous characteristics of operation of the actuating apparatus; previous characteristics of operation of the application apparatus. Alternatively or in addition the data stored on the further apparatus may comprise phenotype data such as gender, age and ethnic origin. Data on skin characteristics of plural different classes of subject such as in respect of age group and/or recognised skin type may be stored. A user of the apparatus may select data for one of the plural classes which most closely matches her characteristics. Alternatively or in addition the data stored on the further apparatus may comprise data operative to provide for operation of at least one of the actuating apparatus and the application apparatus in a particular fashion, such as in respect of a subject belonging to a particular phenotype. Alternatively or in addition the data stored on the further apparatus may comprise skin property data such as skin impedance data.

The data storage may be operative to store data which provides for control of the apparatus for topical application of material in a predetermined fashion. Control may be in respect of at least one of the actuating apparatus and the application apparatus. The data may be configured to effect control to take account of at least one predetermined condition, for example a subject belonging to a particular group such as the subject belonging to a particular phenotype. The application apparatus may, for example, apply a certain amount per se of material for cosmetic purposes or apply material for cosmetic purposes at a particular rate in dependence on the data. Data may be stored in the data storage in dependence on operation of at least one of a user operable control and a data communication port comprised in the apparatus for topical application of material.

The apparatus for topical application of material may be configured to store, such as in data storage, data relating to operation of at least one of the measurement apparatus, the actuating apparatus and the application apparatus. The apparatus for topical application of material may thus be operative to store a profile of operation of apparatus for topical application of material. The apparatus for topical application of material may be configured to take such stored data into account during subsequent operation of the apparatus for topical application of material. Where the apparatus for topical application of material comprises a data communication port, the apparatus for topical application of material may be configured to provide for transmission of stored data from the apparatus for topical application of material by way of the data communication port to further apparatus, such as a computer.

According to a second aspect of the present invention there is provided a method of topically applying material for cosmetic purposes, the method comprising:

measuring a property of skin of a human or animal subject with measurement apparatus;

changing a permeability of the skin of the human or animal subject with actuating apparatus in dependence on the measured property of the skin; and applying material for cosmetic purposes to the skin with application apparatus whilst substantially no iontophoretic current flows through the skin and after the permeability of the skin has been changed.

The method may further comprise physical treatment of the skin. Physical treatment of the skin may comprise at least one of skin abrasion and skin stripping. Physical treatment may be carried out after the step of measuring a property of skin. Further embodiments of the second aspect of the present invention may comprise one or more features of the first aspect of the present invention.

According to a further aspect of the present invention there is provided apparatus for topical application of material, the apparatus comprising: measurement apparatus configured to measure a property of skin of a human or animal subject; actuating apparatus configured to change a property of the skin of the human or animal subject in dependence on the measured property of the skin; and application apparatus configured to apply material to the skin whilst substantially no iontophoretic current flows through the skin and after the property of the skin has been changed. Embodiments of the further aspect of the present invention may comprise one or more features of any previous aspect of the present invention.

According to a yet further aspect of the present invention there is provided a method of topically applying material, the method comprising: measuring a property of skin of a human or animal subject with measurement apparatus; changing a property of the skin of the human or animal subject with actuating apparatus in dependence on the measured property of the skin; and applying material to the skin with application apparatus whilst substantially no iontophoretic current flows through the skin and after the property of the skin has been changed. Embodiments of the yet further aspect of the present invention may comprise one or more features of any previous aspect of the present invention.

According to another aspect of the present invention there is provided apparatus for topical application of material, the apparatus comprising: measurement apparatus configured to measure a property of skin of a human or animal subject; actuating apparatus configured to change a property of the skin of the human or animal subject; and application apparatus configured to apply material to the skin. According to another aspect of the present invention there is provided a method of topically applying material, the method comprising: measuring a property of skin of a human or animal subject with measurement apparatus; changing a property of the skin of the human or animal subject with actuating apparatus; and applying material to the skin with application apparatus. Embodiments of either one of these aspects of the present invention may comprise one or more features of any previous aspect of the present invention.

BRIEF DESCRIPTION OF DRAWINGS

Further features and advantages of the present invention will become apparent from the following specific description, which is given by way of example only and with reference to the accompanying drawings, in which.

DESCRIPTION OF EMBODIMENTS

Figure 1:
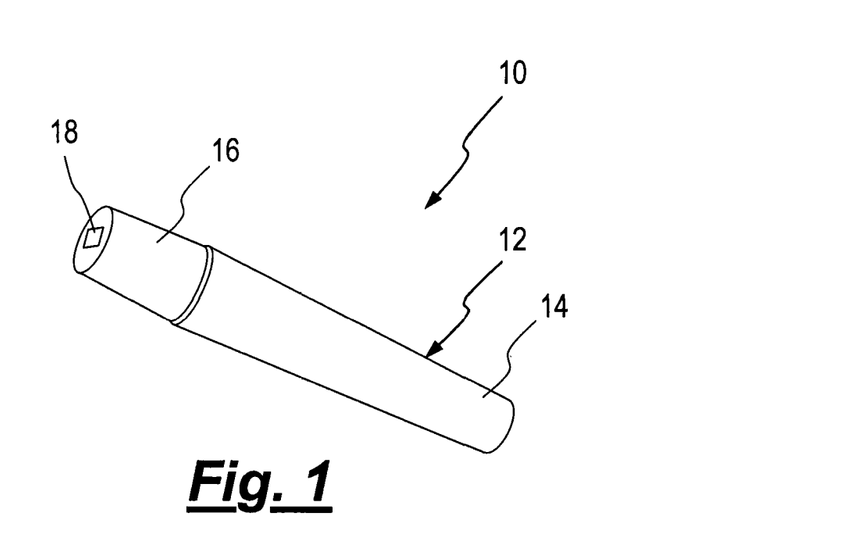
FIG. 1 is a schematic of apparatus for topical application of material according to the present invention.

A schematic of apparatus for topical application of material 10 is shown in FIG. 1. The apparatus comprises a housing 12 which supports and contains components of the apparatus and defines an external surface of the apparatus. The housing comprises two parts: a main body 14; and an operative body 16. The housing is of a shape and size that the main body may be gripped in the hand of a user. The main body 14 contains and supports a reservoir (not shown) which contains a cosmetic agent such as skin-care lotion (which constitutes material for cosmetic purposes). The main body 14 also contains and supports six rechargeable AA NiMH battery cells which provide electrical power for the apparatus 10. The battery cells are rechargeable by way of an external battery charger in accordance with conventional practice. The operative body 16 comprises electronic and electro-mechanical components of the apparatus 10. The electronic and electro-mechanical components are described below with reference to FIG. 2. The distal end of the operative body 16 defines a substantially planar surface on which an electrode assembly 18 is mounted. The electrode assembly 18 is described below in with reference to FIG. 2 and subsequently in more detail with reference to FIG. 3.

Figure 2:
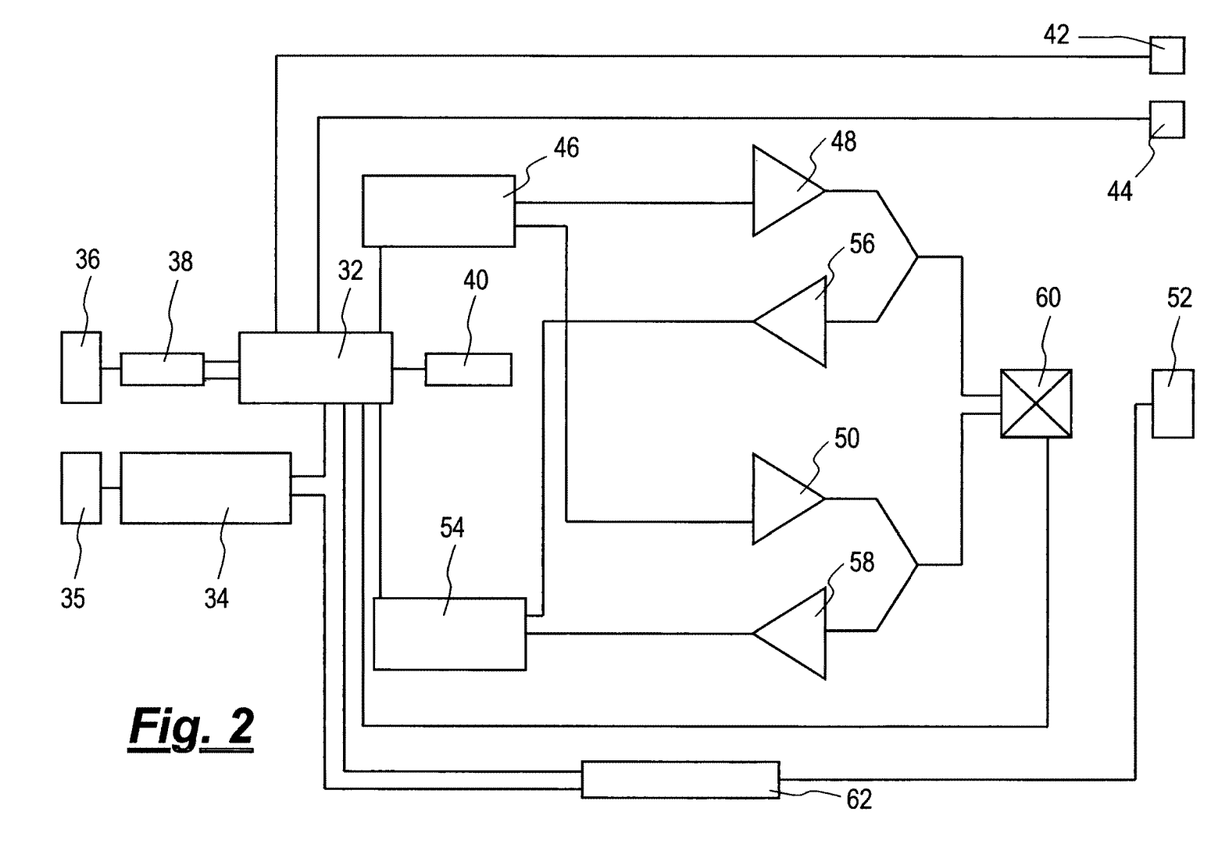
FIG. 2 is a block diagram of the main operative components of the apparatus of FIG. 1.

A block diagram of the main operative components of the apparatus of FIG. 1 is shown in FIG. 2. The main operative components comprise an ARM Cortex M3 embedded processor 32, electrical power supply circuitry 34, a USB communication port 36, communication port driver circuitry 38, a loudspeaker 40, LED indicators 42 and an on-off switch 44. The ARM Cortex M3 embedded processor 32 is operative to control operation of the apparatus 10 of FIG. 1 in respect of measurement, actuation and application of cosmetic agent as is described further below. The ARM Cortex M3 embedded processor 32 is therefore operative to store in integral memory firmware to control such operation and to provide for control and operation as otherwise described herein. The provision of such firmware is within the ordinary design capabilities of the notionally skilled person. The ARM Cortex M3 embedded processor 32 comprises integral components such as timers, an analogue-to-digital converter, and a digital-to-analogue converter and plural digital input/output lines. The analogue-to-digital converter is operative to provide for analogue-to-digital conversion of acquired analogue signals for processing within the ARM Cortex M3 embedded processor 32. The digital-to-analogue converter is operative to convert digital data to analogue signals for the actuating apparatus described below. The digital input/output lines are operative to control components of the apparatus 10, such as in respect of putting electronic components into a tri-state condition or into or out of a power conserving mode, and provide for control of whatever further external apparatus may be provided, such as skin abrading apparatus.

The electrical power supply circuitry 34 comprises the electric batteries described above with reference to FIG. 1, and is otherwise configured by way of bandgap reference circuitry and voltage generation and regulation circuitry to provide electrical power rails for the electronic circuitry and required reference voltages. The electric batteries are recharged when recharging current is provided by way of gold plated copper terminals 35 provided on the exterior of the housing 12. The design of electrical power supply circuitry 34 is within the ordinary design capabilities of the notionally skilled person. The loudspeaker 40 is operative under control of the ARM Cortex M3 embedded processor 32 to provide audible notification as to when components of the apparatus 10 of FIG. 1, such as the measurement apparatus and the actuating apparatus, are operating. The LED indicators 42 are operative under control of the ARM Cortex M3 embedded processor 32 to provide visible notification as to when the apparatus 10 of FIG. 1 is switched on and otherwise, such as by use of different colours, to provide visible notification as to when different parts of the apparatus 10 of FIG. 1 are operating, such as when each of the measurement apparatus and the actuating apparatus is operating. The communication port driver circuitry 38, which is under control of the ARM Cortex M3 embedded processor 32, drives the USB communication port 36 to provide for reception of data by and transmission of data from the apparatus 10 of FIG. 1 as is described in more detail below. In alternative forms, the communication port driver circuitry 38 is operative to drive a WiFi transceiver to provide for wireless communication of data to and from the apparatus. Design of the apparatus to provide for WiFi communication will be a matter of ordinary design for the skilled reader. The apparatus 10 of FIG. 1 is brought into data communication with a computer, such as a laptop, by way of a USB cable which is connected to the USB communication port 36.

The main operative components of FIG. 2 further comprise a signal generator 46, actuation signal conversion and conditioning circuitry 48, measurement signal conversion and conditioning circuitry 50 and the electrode assembly 18, 52. The signal generator 46 is under control of and receives data from the ARM Cortex M3 embedded processor 32 and is operative to drive each of the actuation signal conversion and conditioning circuitry 48 and measurement signal conversion and conditioning circuitry 50 at different times. The signal generator 46 is operative to determine voltage and current amplitude, frequency, duty cycle and duration of signals generated. The actuation signal conversion and conditioning circuitry 48 comprises a 12-bit digital-to-analogue converter from Analog Devices, namely an AD5339, and other circuitry to provide for current limit control and voltage compliance control depending on the mode of operation and to interface with the electrode arrangement 52. The measurement signal conversion and conditioning circuitry 50 comprises a digital sinewave generator, namely an AD9832 from Analog Devices, a 25 MHz master clock generator, namely a SG8002DCOHB from Epson, and other circuitry to interface with the electrode arrangement 52.

The main operative components of FIG. 2 yet further comprise a signal measurement arrangement 54, a first measurement interface arrangement 56, and a second measurement interface arrangement 58. The signal measurement arrangement 54 comprises an 18-bit analogue-to-digital converter, namely an MCP3421 from Microchip, and is under control of and provides digital data to the ARM Cortex M3 embedded processor 32 in dependence on analogue signals received from the first measurement interface arrangement 56 and the second measurement interface arrangement 58 at different times. The signal measurement arrangement 54 is operative to determine voltage amplitude and phase angle and current amplitude and phase angle. The first measurement interface arrangement 56, comprises circuitry to interface with the electrode arrangement 52. The second measurement interface arrangement 58 comprises circuitry to interface with the electrode assembly 52. In addition the main operative components of FIG. 2 comprise an electrode assembly switching control 60 and a pump arrangement 62. The electrode assembly switching control 60 is under the control of the ARM Cortex M3 embedded processor 32 and is operative to determine the mode of operation of the electrode assembly 52 as is described further below. The pump arrangement 62 is under the control of the ARM Cortex M3 embedded processor 32 and is operative to pump cosmetic agent contained in the reservoir of the apparatus 10 of FIG. 1. A conduit from the reservoir is operative to convey pumped cosmetic agent to an aperture beside the electrode assembly 52 whereby cosmetic agent is dispensed from the apparatus 10 of FIG. 1.

Figure 3:
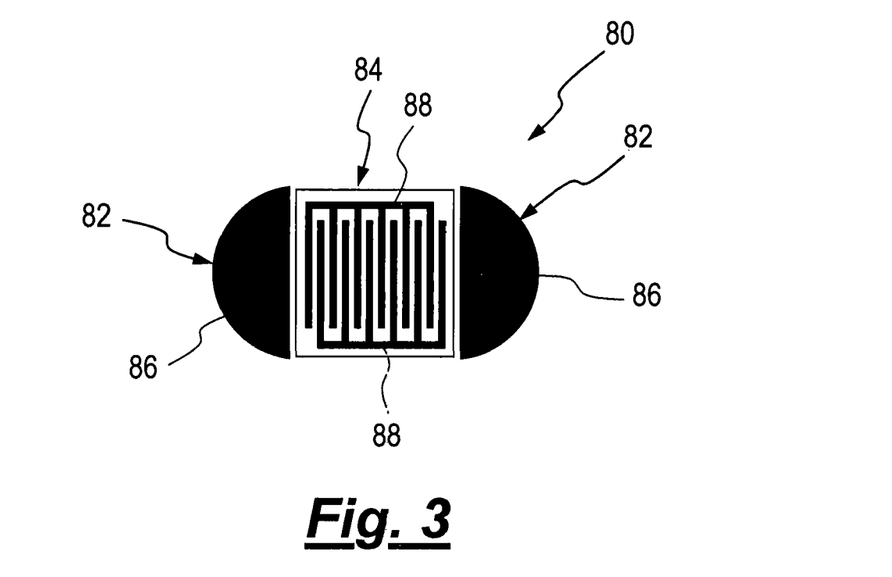
FIG. 3 shows an electrode assembly comprised in the apparatus of FIG. 1.

The electrode assembly 18, 52 of FIGS. 1 and 2 is shown in more detail in FIG. 3. The electrode assembly 80 of FIG. 3 comprises a first electrode arrangement 82 and a second electrode arrangement 84. The first electrode arrangement 82 comprises two first electrodes 86 which are spaced apart from each other such that the second electrode arrangement 84 is disposed therebetween. The two first electrodes 86 lie in substantially the same plane, each define a semicircle in area and are disposed such that the linear bases of the semicircles face each other. The two first electrodes 86 are formed of gold plated copper and are not covered by an insulating material. The second electrode arrangement 84 comprises two second electrodes 88 which each define serpentine paths and are disposed relative to each other such that they define an interdigitated structure. The two second electrodes 88 lie in substantially the same plane and in the same plane as the two first electrodes 86. The two second electrodes 88 are formed of gold plated copper. A layer of an insulating material, such as polyurethane, covers the two second electrodes 88. The width of each of the two second electrodes 88 is 0.1 mm and the separation between the two second electrodes 88 is 0.06 mm. Different electrode spacings are used depending on the thickness of the skin to which the cosmetic is to be applied. An electrode spacing of 0.06 mm is appropriate where the stratum corneum is thin, such as around the eye. An electrode spacing nearer to 0.1 mm is appropriate where the stratum corneum is thicker, such as the heel. The total area of the electrode assembly 80 is 2 cm$^2$ (2 cm long by 1 cm wide).

Figure 4A:
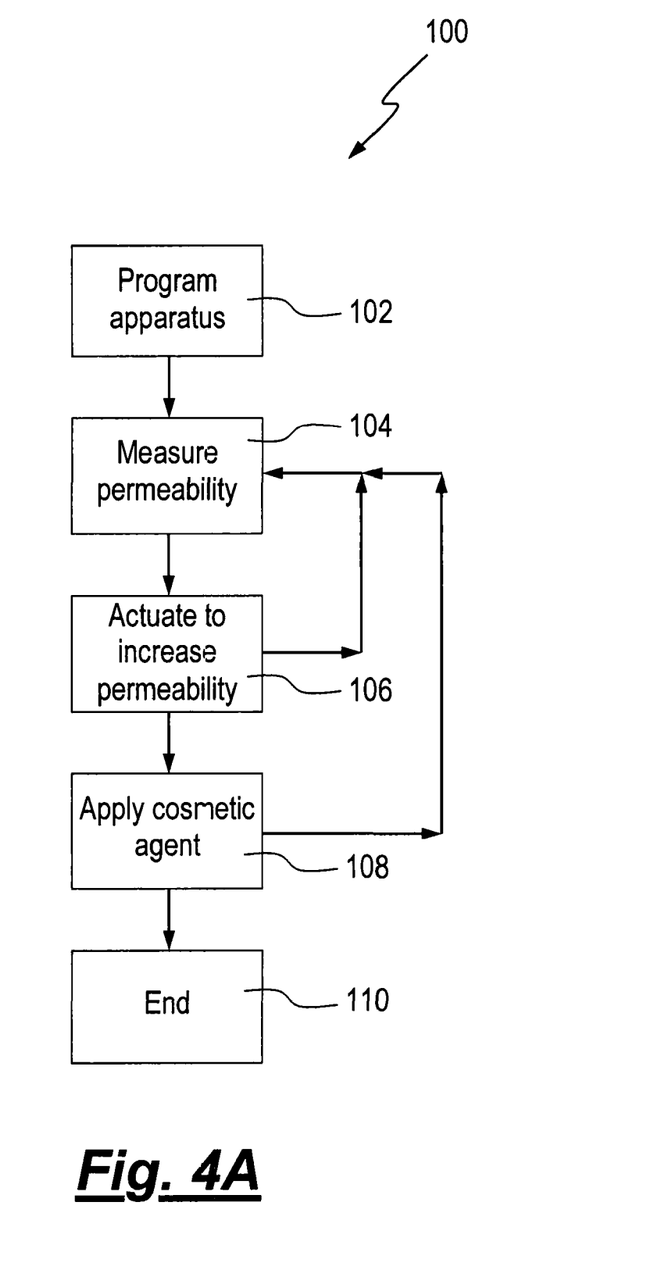
FIG. 4A is a flow chart showing the main steps during operation of the apparatus of FIG. 1.

Operation of the apparatus described above with reference to FIGS. 1 to 3 will now be described with reference to the flow chart 100 shown in FIG. 4A. After the apparatus 10 of FIG. 1 is switched on by way of the on/off switch 44 the apparatus is programmed 102. Programming the apparatus comprises configuring the apparatus to carry out a skin preparation and cosmetic agent application regime. The apparatus is configured by downloading configuration data from a computer which stores the configuration data by way of a USB cable to the USB communication port 36 and thereafter to the ARM Cortex M3 embedded processor 32 for storage therein. The configuration data comprises phenotype data such as gender, age and ethnic origin and also skin type data such as normal, dry, oily and combination. The user makes an appropriate selection on the computer before the configuration data is downloaded. The configuration data also comprises historic data which has been uploaded from previous use of the apparatus 10 of FIG. 1, with such historic data being operative to provide for refining of the skin preparation and cosmetic agent application regime. According to one approach, frequency of use of the apparatus and the amount of cosmetic agent dispensed on each occasion is stored. The processor 32 is operative in dependence on the stored data to restrict the amount of cosmetic agent dispensed during further use of the apparatus. For example a maximum weekly dose for a particular cosmetic agent may be 2 ml based on previous use. The processor 32 is therefore operative to provide that no more than this amount is dispensed in a seven day period or to reduce the amount dispensed during the latter part of the seven day period. If a user does not use the apparatus for one or more days during a seven day period the processor is operative to increase the amount dispensed during the remaining days of the seven day period. According to another approach, historic data provides for distinguishing between trends and isolated events. The historic data comprises environmental factors such as temperature and humidity. Such factors affect skin characteristics such as a skin moisture content and permeability. Historic temperature and humidity data allows the present skin measurements to be applied in the context of presently measured temperature and humidity. For example, if presently measured temperature and humidity are very low this indicates that skin impedance measurements are higher than they would be otherwise whereby high impedance measurements are a consequence of current environment rather than poor skin health. The processor 32 is therefore operative to adjust present skin impedance measurements to take account of presently measured temperature and humidity whereby an appropriately lower amount of cosmetic product is dispensed.

The second stage comprises measurement of the permeability of the skin 104 during which the electrode assembly 18 is brought into contact with the skin. Two forms of measurement are made: skin impedance measurement; and skin capacitance measurement. Each form of measurement will now be described in turn although the two forms of measurement are both used to provide enhanced characterisation of skin permeability.

Figure 4B:
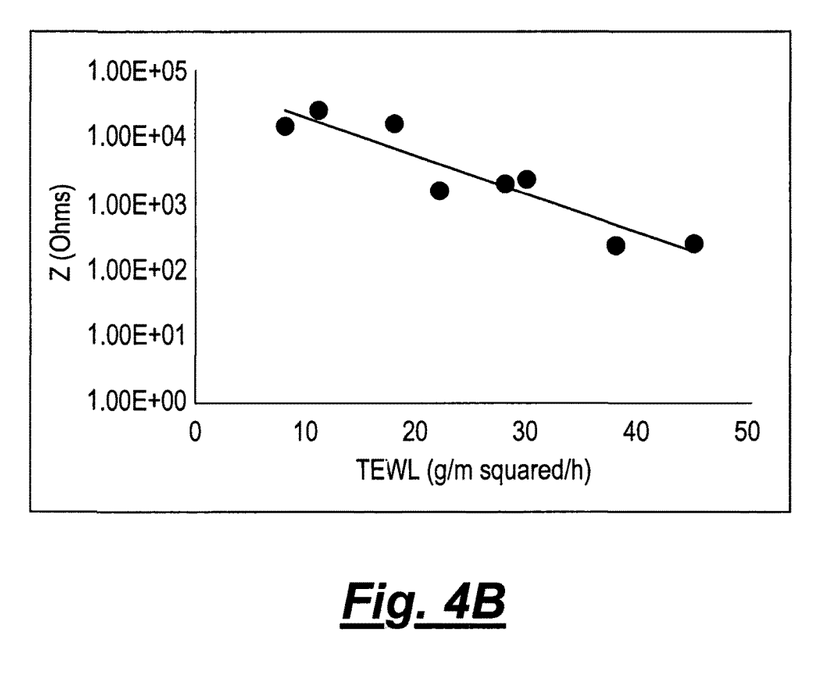
FIG. 4B is a graph of skin impedance against rate of transepidermal water loss.

Considering skin impedance measurement first, the signal generator 46, the measurement signal conversion and conditioning circuitry 50 and the first electrode arrangement 82 are operative together under control of the ARM Cortex M3 embedded processor 32 to apply an alternating current signal of swept frequency between 100 Hz and 1 MHz or an alternating current signal comprising frequencies between 100 Hz and 1 MHz. The signal measurement arrangement 54, the second measurement interface arrangement 58 and the first electrode arrangement 82 are operative together under control of the ARM Cortex M3 embedded processor 32 to measure the current signal between the electrodes of the first electrode arrangement 82 at different frequencies. The ARM Cortex M3 embedded processor 32 is operative to determine the impedance on the basis of the current measurements and the applied voltage and then to determine the real and imaginary parts of the impedance. The thus determined real part of the impedance is then correlated with skin permeability by the ARM Cortex M3 embedded processor 32 in dependence on a model stored in the processor 32. A graph which relates skin impedance to transepidermal water loss is shown in FIG. 4B. The graph of FIG. 4B forms the basis for a model that relates impedance to skin permeability. The graph of FIG. 4B and the model based thereon are described further below. The ARM Cortex M3 embedded processor 32 is further operative to determine a capacitance of the skin in dependence on the imaginary part of the impedance, the frequency of the applied signal and a resistance value representing resistance of an outermost layer of the stratum corneum in accordance with the model of the skin described below with reference to FIGS. 5A and 5B.

Turning now to consider skin capacitance measurement, the signal generator 46, measurement signal conversion and conditioning circuitry 50 and the second electrode arrangement 84 are operative together under control of the ARM Cortex M3 embedded processor 32 to apply an electric field to the skin. More specifically the electrodes of the second electrode arrangement 84 are operative as plate of a capacitor with the skin constituting the dielectric between the plates of the capacitor. The signal generator 46 is operative to provide for application of a signal of alternating current form to the electrodes of the second electrode arrangement 84. The signal measurement arrangement 54 and the second measurement interface arrangement 58 are operative together under control of the ARM Cortex M3 embedded processor 32 to provide for measurement of the current and voltage between the electrodes of the second electrode arrangement 84. The ARM Cortex M3 embedded processor 32 is operative to determine the capacitive reactance and then relative permittivity in dependence thereon. The ARM Cortex M3 embedded processor 32 is also operative to provide for determination the thickness of the skin. Determination of relative permittivity and of skin thickness will now be described further below.

The reactance of the capacitor defined by the electrode plates of the second electrode arrangement 84 and the skin is given by:

$$X_C = \frac{1}{2\pi f C}$$

Re-arranging we obtain:

$$C = \frac{1}{2\pi f X_c}$$

The capacitance is related to the permittivity of the material between the plates by:

$$C = \varepsilon \frac{A}{d}$$

Combining the two immediately preceding equations and making c, the relative permittivity, the subject of the combined equation we obtain:

$$\varepsilon = \frac{d}{2\pi f X_c A}$$

A, the area of the plates and f, the frequency, are known. As mentioned above, the capacitive reactance, $X_c$, is measured and thus known. The distance separating the plates, d, is estimated based on the typical thickness of the part of the skin being measured. The relative permittivity, c, is therefore calculated.

As described above, measurement using the first electrode arrangement 82 also provides for determination of the capacitance C. In view of capacitance being related to relative permittivity by:

$$C = \varepsilon \frac{A}{d}$$

We re-arrange to obtain:

$$d = \varepsilon \frac{A}{C}$$

The capacitance, C, is provided by measurement with the first electrode arrangement 82, the relative permittivity, $\varepsilon$, is provided by measurement with the second electrode arrangement 84 and the area, A, of the second electrode arrangement is known. Hence d, the plate separation or more specifically the depth of the stratum corneum, is calculated to thereby provide a more accurate value for d.

Returning now to FIG. 4A now that the permeability of the skin has been determined, the ARM Cortex M3 embedded processor 32 is operative to determine whether or not the permeability meets the requirements stored at the first stage 102 of the process. If not, the process progresses to a step in which the permeability of the skin is increased 106. The permeability of the skin is increased by two approaches: application of an electric potential signal; and application of an electric current signal. Each approach will now be described in turn although the two approaches are both used to provide for an enhanced increase in permeability of the skin.

Considering application of an electric potential signal first, the signal generator 46, the actuation signal conversion and conditioning circuitry 48 and the second electrode arrangement 84 are operative together under control of the ARM Cortex M3 embedded processor 32 to apply an electric potential in the range of 20 volts to 140 volts in the form of a pulse of duration of 10 μs to 10 ms. The pulse is operative to reversibly form plural pathways through the stratum corneum to thereby increase permeability. During application of the electric potential, the signal measurement arrangement 54 and the first measurement interface arrangement 56 are operative to measure the electric potential at the second electrode arrangement 84 to monitor the applied electric potential and provide feedback control.

Turning now to consider the application of an electric current signal, the signal generator 46, the actuation signal conversion and conditioning circuitry 48 and the first electrode arrangement 82 are operative together under control of the ARM Cortex M3 embedded processor 32 to apply a substantially constant current to the skin by way of the electrodes of the first electrode arrangement 82. A potential of no more than 50 Volts and a current of up to 500 μA/cm² are applied to the skin. During application of the current, the signal measurement arrangement 54 and the first measurement interface arrangement 56 are operative to measure the current at the first electrode arrangement 82 to monitor the applied current and provide feedback control. Application of the current is operative to maintain the pathways formed by the pulsed electric potential in the absence of the latter.

After step 106 of FIG. 4A, the apparatus 10 of FIG. 1 is operative to measure the permeability as described above with reference to step 104 of FIG. 4A. Steps 106 and 104 are repeated until a desired permeability is achieved.

When a desired permeability is achieved, operation of the apparatus 10 of FIG. 1 progresses to application of the cosmetic agent to the skin 108. More specifically the pump arrangement 62 is operative under control of the ARM Cortex M3 embedded processor 32 to pump cosmetic agent from the reservoir through the aperture provided adjacent the electrode assembly 18 onto the skin. The amount and rate of application of cosmetic agent to the skin is determined in accordance with data stored in the ARM Cortex M3 embedded processor 32 at step 102 in FIG. 4A to meet a desired cosmetic application regime. In certain forms, application of cosmetic agent takes place in plural stages with measurement performed in accordance with step 104 and actuation in accordance with step 106 performed between stages of application of cosmetic agent.

When application of cosmetic agent is complete 110, data relating to the just completed skin preparation and cosmetic agent application process is stored by the ARM Cortex M3 embedded processor 32 for later transmission to the user's computer. As described above such historic data is used in subsequent treatments.

FIG. 4B shows a graph which relates skin impedance to the rate of transepidermal water loss (TEWL). Transepidermal water loss is a measurement of water lost through the skin by way of the stratum corneum other than by sweating. As per FIG. 4B, the units of water loss are expressed in g/m²/h (grams per meter squared per hour). As can be seen from FIG. 4B, there is a generally linear relationship between the log of skin impedance and the rate of transepidermal water loss with impedance decreasing as the rate of transepidermal water loss increases. It is known that the rate of transepidermal water loss corresponds to skin permeability. The model used by the ARM Cortex M3 embedded processor 32 in determining skin permeability is based on the relationship of FIG. 4B between skin impedance and the rate of transepidermal water loss.

Figure 5A:
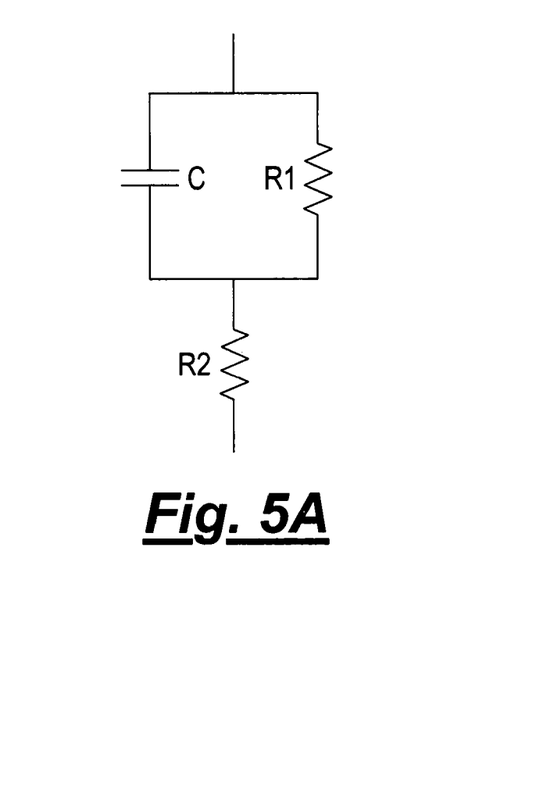
FIG. 5A is an example of an electrical equivalent model of the stratum corneum.
Figure 5B:
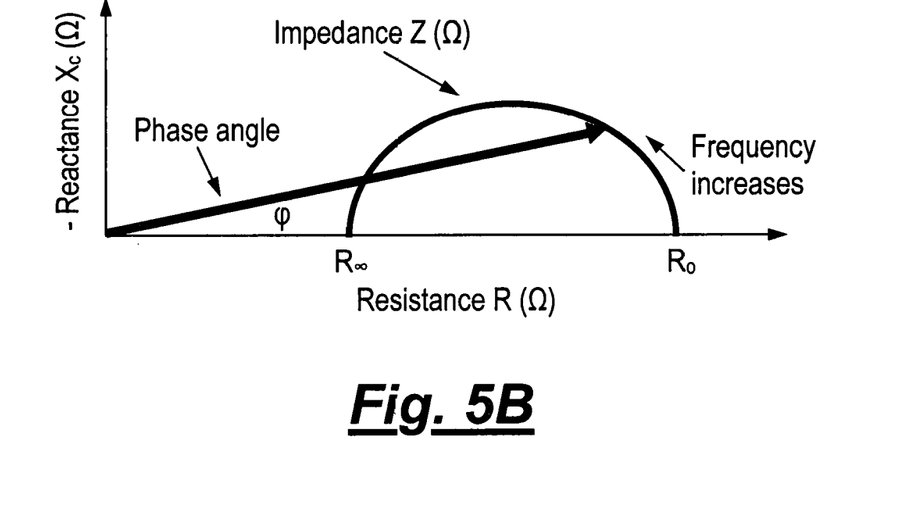
FIG. 5B is a representative Cole-Cole plot for skin tissue.

A simple electrical equivalent model of the stratum corneum 120 is shown in FIG. 5A. The model consists of a first resistor $R_1$ in parallel with a capacitor C with this parallel arrangement being in series with a second resistor $R_2$. C and $R_1$ represent the capacitance and resistance of the outermost layer of the stratum corneum and $R_2$ represents the resistance found in deeper layers of the stratum corneum. Typical values for $R_1$ range from 100Ω to 5 MΩ cm² and $R_2$ from 0.1Ω to 1 kΩ cm². The model reflects the frequency dependence of skin and in particular the decrease in magnitude of the impedance as frequency increases. Based on skin impedance measurements as described above and the theory for biological tissues according to the Cole brothers (Bioelectrical impedance analysis—part I: review of principles and methods, Kyle, U. G., I. Bosaeus, et al. (2004), Clinical Nutrition 23(5): 1226-1243), values for $R_1$, $R_2$ and C can be calculated. A typical complex plot obtained when impedance of any biological tissue is analysed is shown in FIG. 5B. According to the Cole brothers' empirical equation the impedance is given by:

$$Z = R_\infty + \frac{R_0 - R_\infty}{1 + (j\omega\tau)^\alpha} \quad \text{Equation 1}$$

Where $R_\infty$ is the resistance at very high frequencies where the semicircle of FIG. 5B crosses the x axis (i.e. when the reactance is zero), $R_0$ is the resistance at very low frequencies where the semicircle of FIG. 5B crosses the x axis (i.e. when the reactance is zero), ω is the angular frequency, T is a time constant and $\varphi = \alpha(\pi/2)$ is the constant phase angle. The general equation for this circuit can be written as:

$$Z = Z_{series} + Z_{parallel} \quad \text{Equation 2}$$

Based on a comparison of Equation 1 with Equation 2 the following equations can be obtained:

$$Z_{series} = R_\infty = R_2 \qquad \text{Equation 3}$$

$$Z_{parallel} = \frac{R_0 - R_\infty}{1 + (j\omega t)^\alpha} = \frac{R_1}{1 + j\omega R_1 C} \qquad \text{Equation 4}$$

The parallel impedance has real and imaginary parts and can be represented in the Cartesian form as:

$$Z_{parallel} = Z' + Z'' = \frac{R_1}{1 + \omega^2 R_1^2 C^2} - j\frac{\omega R_1^2 C}{1 + \omega^2 R_1^2 C^2} \qquad \text{Equation 5}$$

In Equation 5 Z" is the part of interest which provides for calculation of the value of C:

$$Z'' = j\frac{\omega R_1^2 C}{1 + \omega^2 R_1^2 C^2} \qquad \text{Equation 6}$$

where Z" is measured, $\omega$ is known and $R_1$ is $R_0$ at low frequencies or $R_\infty$ at high frequencies. Equation 6 is solved for C in view of Z", $R_1$ and $\omega$ being known.

The invention claimed is:

1. Apparatus for topical application and intradermal delivery of material for cosmetic or medical purposes, the apparatus comprising:
   a processor;
   a measurement apparatus controlled by the processor to measure a property of skin of a human or animal subject, wherein the measurement apparatus comprises spaced apart measurement electrodes, a signal generator and a signal measurement arrangement, the signal generator applying a measurement signal to the spaced apart measurement electrodes, and the signal measurement arrangement measuring a signal between the spaced apart measurement electrodes;
   an actuating apparatus controlled by the processor to change a permeability of the skin of the human or animal subject in dependence on the measured property of the skin, wherein the actuating apparatus comprises spaced apart actuating electrodes and the signal generator, the signal generator applying an actuating signal to the spaced apart actuating electrodes whereby the spaced apart actuating electrodes apply an electric signal to the skin sufficient to induce electroporation but insufficient to cause irreversible change in permeability of the skin;
   an application apparatus controlled by the processor to apply material for cosmetic or medical purposes to the skin when the measurement apparatus stops applying the measurement signal to the skin and when the actuating apparatus stops applying the actuating signal to the skin whereby no iontophoretic current flows in the skin and after the permeability of the skin has been changed, wherein the application apparatus comprises an electric pump that applies the material for cosmetic or medical purposes from a reservoir via a conduit, and wherein the application apparatus applies the material intradermally in dependence on the electroporation induced by the actuating apparatus; and
   a housing containing the measurement apparatus, the actuating apparatus and the application apparatus, in which the spaced apart actuating electrodes are disposed in substantially the same plane and are mounted on a substantially planar surface of an end of the housing whereby the spaced apart actuating electrodes and the end of the housing form a substantially planar surface that can abut against the skin;
   in which the electric signal applied to the skin by the actuating apparatus comprises: an electric potential signal causing no current flow in the skin; and an electric current signal causing flow of an electric current in the skin; and
   in which the actuating apparatus comprises first spaced apart actuating electrodes and second spaced apart actuating electrodes, the first spaced apart actuating electrodes are electrically isolated from the skin when the actuating apparatus bears against the skin, the second spaced apart actuating electrodes lack electrical isolation from the skin, the first spaced apart actuating electrodes applying the electric potential signal to the skin, and the second spaced apart actuating electrodes applying the electric current signal to the skin.

2. Apparatus according to claim 1 in which the electric signal applied to the skin by the actuating apparatus is varying.

3. Apparatus according to claim 1 in which the electric potential signal and the electric current signal are applied to the skin by the actuating apparatus at different times.

4. Apparatus according to claim 1 in which the electric potential signal has the form of a pulse, the pulse decaying progressively from a peak value.

5. Apparatus according to claim 1 in which the second spaced apart actuating electrodes carry an electric current and pass the electric current therebetween by way of the skin when the second spaced apart actuating electrodes are in contact with the skin.

6. Apparatus according to claim 5 in which the signal generator is operative such that the electric current passing between the second spaced apart actuating electrodes is not pulsed.

7. Apparatus according to claim 5 comprising current control circuitry measuring the electric current carried by the second spaced apart actuating electrodes and controlling the electric current passing between the second spaced apart actuating electrodes in dependence on the measured current.

8. Apparatus according to claim 1 in which the signal measurement arrangement measures an impedance of the skin.

9. Apparatus according to claim 8 operative to make a determination in respect of permeability of the measured skin in dependence on a real part of measured impedance.

10. Apparatus according to claim 9 operative to make the determination in dependence on a model which relates measured impedance and permeability to each other.

11. Apparatus according to claim 1 in which the housing contains and supports components of the apparatus, the housing being configured to be gripped in one hand.

12. Apparatus according to claim 1 configured to measure a property of the skin by way of the measurement apparatus before and after the actuating apparatus is operative.

13. Apparatus according to claim 1 configured to at least one of measure a property of the skin and change a permeability of the skin after operation of the application apparatus.

14. Apparatus according to claim 1 comprising data storage, data stored therein being from previous operation of the apparatus for application of material in respect of at least one of: previous measurement by the measuring apparatus; previous characteristics of operation of the actuating apparatus; previous characteristics of operation of the application apparatus.

15. Apparatus according to claim 1 in which the electric signal comprises an electric current of no more than 50 $\mu A/cm^2$ while the electric signal is being applied to the skin.

16. Apparatus according to claim 1 in which the electric signal comprises an electric current of at least 1 $\mu A/cm^2$ while the electric signal is being applied to the skin.

17. Apparatus according to claim 1 in which the application apparatus applies material for cosmetic or medical purposes to the skin after the permeability of the skin has been changed to a desired permeability.

18. Apparatus for topical application and intradermal delivery of material for cosmetic or medical purposes, the apparatus comprising:
   a processor;
   a measurement apparatus controlled by the processor to measure a property of skin of a human or animal subject, wherein the measurement apparatus comprises spaced apart measurement electrodes, a signal generator and a signal measurement arrangement, the signal generator applying a measurement signal to the spaced apart measurement electrodes, and the signal measurement arrangement measuring a signal between the spaced apart measurement electrodes;
   an actuating apparatus controlled by the processor to change a permeability of the skin of the human or animal subject in dependence on the measured property of the skin, wherein the actuating apparatus comprises spaced apart actuating electrodes and the signal generator, the signal generator applying an actuating signal to the spaced apart actuating electrodes whereby the spaced apart actuating electrodes apply an electric signal to the skin sufficient to induce electroporation but insufficient to cause irreversible change in permeability of the skin;
   an application apparatus controlled by the processor to apply material for cosmetic or medical purposes to the skin when the measurement apparatus stops applying the measurement signal to the skin and when the actuating apparatus stops applying the actuating signal to the skin whereby no iontophoretic current flows in the skin and after the permeability of the skin has been changed, wherein the application apparatus comprises an electric pump that applies the material for cosmetic or medical purposes from a reservoir via a conduit, and wherein the application apparatus applies the material intradermally in dependence on the electroporation induced by the actuating apparatus;
   in which the electric signal applied to the skin by the actuating apparatus comprises: an electric potential signal causing no current flow in the skin; and an electric current signal causing flow of an electric current in the skin; and the electric potential signal and the electric current signal are applied to the skin by the actuating apparatus at different times; and
   in which the actuating apparatus comprises first spaced apart actuating electrodes and second spaced apart actuating electrodes, the first spaced apart actuating electrodes are electrically isolated from the skin when the actuating apparatus bears against the skin, the second spaced apart actuating electrodes lack electrical isolation from the skin, the first spaced apart actuating electrodes applying the electric potential signal to the skin, and the second spaced apart actuating electrodes applying the electric current signal to the skin.

19. A method of topically applying and intradermally delivering material for cosmetic or medical purposes, the method comprising:
   measuring a property of skin of a human or animal subject with a measurement apparatus controlled by a processor, wherein the measurement apparatus comprises spaced apart measurement electrodes, a signal generator and a signal measurement arrangement, the signal generator applying a measurement signal to the spaced apart measurement electrodes, and the signal measurement arrangement measuring a signal between the spaced apart measurement electrodes;
   changing a permeability of the skin of the human or animal subject with an actuating apparatus controlled by the processor and in dependence on the measured property of the skin, wherein the actuating apparatus comprises spaced apart actuating electrodes and the signal generator, the signal generator applying an actuating signal to the spaced apart actuating electrodes whereby the spaced apart actuating electrodes apply an electric signal to the skin sufficient to induce electroporation but insufficient to cause irreversible change in permeability of the skin; and
   applying material for cosmetic or medical purposes to the skin with an application apparatus controlled by the processor and when the measurement apparatus stops applying the measurement signal to the skin and when the actuating apparatus stops applying the actuating signal to the skin whereby no iontophoretic current flows in the skin and after the permeability of the skin has been changed, wherein the application apparatus comprises an electric pump that applies the material for cosmetic or medical purposes from a reservoir via a conduit, and wherein the application apparatus applies the material intradermally in dependence on the electroporation induced by the actuating apparatus;
   in which a housing contains the measurement apparatus, the actuating apparatus and the application apparatus, in which the spaced apart actuating electrodes are disposed in substantially the same plane and are mounted on a substantially planar surface of an end of the housing whereby the spaced apart actuating electrodes and the end of the housing form a substantially planar surface that can abut against the skin;
   in which the electric signal applied to the skin by the actuating apparatus comprises: an electric potential signal causing no current flow in the skin; and an electric current signal causing flow of an electric current in the skin; and
   in which the actuating apparatus comprises first spaced apart actuating electrodes and second spaced apart actuating electrodes, the first spaced apart actuating electrodes are electrically isolated from the skin when the actuating apparatus bears against the skin, the second spaced apart actuating electrodes lack electrical isolation from the skin, the first spaced apart actuating electrodes applying the electric potential signal to the skin, and the second spaced apart actuating electrodes applying the electric current signal to the skin.

* * * * *